United States Patent [19]

Slaugh

[11] 4,358,628
[45] Nov. 9, 1982

[54] ALKYLATION OF BENZENE COMPOUNDS WITH DETERGENT RANGE OLEFINS
[75] Inventor: Lynn H. Slaugh, Houston, Tex.
[73] Assignee: Shell Oil Company, Houston, Tex.
[21] Appl. No.: 277,514
[22] Filed: Jun. 26, 1981
[51] Int. Cl.$^3$ ................................................ C07C 2/64
[52] U.S. Cl. .................................................... 585/455
[58] Field of Search ........................................ 585/455
[56] References Cited
U.S. PATENT DOCUMENTS 2,882,325  4/1959  Luvisi et al. ......................... 585/460
3,126,423  3/1964  Krönig et al. ........................ 585/466
3,153,677  10/1964 Domash et al. ...................... 585/467
3,346,657  10/1967 Henke et al. ........................ 585/455

Primary Examiner—Curtis R. Davis

[57] ABSTRACT

Benzene compounds are successfully alkylated with detergent range olefins with a very active and very selective catalyst prepared by impregnating a 70–90% silica support with a tungsten salt, calcining the impregnated material and subsequently activating the catalyst in a neutral or reducing atmosphere at a temperature ranging from about 200° C. to about 350° C.

8 Claims, No Drawings

ALKYLATION OF BENZENE COMPOUNDS WITH DETERGENT RANGE OLEFINS

BACKGROUND OF THE INVENTION

1. Field of the Invention

This invention relates to a process for alkylating benzene compounds with detergent range olefins using a tungsten oxide catalyst supported on a silica-alumina support.

2. Background

Alkylated aromatics are important materials that have utility for several applications. For example, the so-called "linear alkyl benzenes", which are benzenes which have been alkylated with detergent range linear olefins, are useful detergent intermediates. At present, these compounds are manufactured by two different processes, namely $AlCl_3$-catalyzed alkylation of aromatics with monochloro-paraffins and HF-catalyzed alkylation with internal olefins. In principle, advantages could result from using a non-corrosive and environmentally attractive heterogeneous catalyst in a fixed-bed mode of operation.

U.S. Pat. No. 3,153,677 issued October 20, 1964, teaches the use of supported tungsten oxide to alkylate benzene compounds with $C_2$ to $C_5$ range olefins. Tungsten oxide materials, however, are generally known as disproportionation catalysts, particularly when used in the presence of detergent-range olefins. See, for example, U.S. Pat. No. 3,261,879 issued July 19, 1966, 3,365,513 issued Jan. 23, 1968 and 3,445,541 issued May 20, 1969. This tendency of tungsten oxide materials to disproportionate higher olefins presents a serious problem when benzene compounds are alkylated with detergent range olefinic materials.

SUMMARY OF THE INVENTION

This invention relates to a process for alkylating benzene and substituted benzenes with a detergent range olefin having a carbon number ranging from about 8 to about 22 by contacting said benzene or substituted benzene with said olefin in the presence of a catalyst comprising tungsten oxide supported on a porous silica-alumina support. The support typically contains from about 70 to about 90% by weight of silica. The catalyst is prepared in a special manner providing for minimal disproportionation by-products. The catalyst is prepared by impregnating the support with an aqueous solution of a water soluble tungsten salt, drying and calcining the impregnated support at a temperature ranging from about 600° C. to about 800° C. and subsequently activating the catalyst in a neutral or reducing gaseous atmosphere at a temperature ranging from about 200° C. to about 400° C.

Catalysts prepared as described above are long-lived and can be utilized to alkylate benzene compounds with the higher range olefins without concomitant disproportionation of the olefins, resulting in a clean alkylation of the benzene compounds. The particular alumina-silica support utilized provides for a higher activity than does the use of other supports such as, for example, alumina or silica.

DESCRIPTION OF THE PREFERRED EMBODIMENTS

The aromatic compound to be alkylated by the process of the instant invention is benzene or a substituted benzene, preferably an alkyl-substituted benzene. Of the alkyl-substituted benzenes, particularly desirable are the mono- and poly-substituted lower alkyl benzenes, wherein the substituted alkyl substituent has a carbon number ranging from 1 to about 5, more particularly ranging from about 1 to 2. Suitable examples include the following as particularly desirable alkylation feedstocks: benzene, toluene, xylenes, ethylbenzene, cumene, n-propylbenzene and other mono- and poly-lower alkyl benzenes. Particularly desirable are benzene, toluene and xylene. Other substituted benzenes can be utilized in the instant process such as for example phenols, halobenzenes, etc. when substituent does not interfere with the alkylation process. The aromatic feedstock can be a single aromatic hydrocarbon or a mixture of two or more aromatic hydrocarbons. The aromatic hydrocarbons can be fed into the reactor neat or mixed in a suitable non-reactive organic solvent such as for example a saturated hydrocarbon.

The olefins employed in the alkylation reaction are olefins in the so-called detergent range, i.e. having carbon numbers ranging from about 8 to about 22, preferably from about 10 to about 20. The olefins may be alpha or internal olefins and may be either straight chain or branched chain olefins. The olefin feedstock can be either a highly purified olefin or a mixture of two or more olefins or a fraction rich in one or more of the olefins and containing also paraffins or other hydrocarbons of similar boiling range.

The catalysts used in the instant process are prepared by impregnating a suitable support with a solution of a tungsten salt, this salt being decomposable upon calcining to a tungsten oxide. The supports used to prepare the catalysts of this invention are the silica-aluminas which are commercially available and generally employed as cracking catalysts. Preferred silica-alumina catalyst supports contain from about 70 to 90% by weight of silica. A particularly valuable commercially available silica catalyst support is the Davison Grade 980–25 (manufactured by Davison Chemical Division, W. R. Grace & Co.). The silica-alumina support can also be prepared in a conventional fashion, as for example by co-precipitation, co-gellation, or by spray drying.

The first step in the preparation of the catalyst is to impregnate the carrier with a tungsten salt which would decompose to the oxide upon heating. The salt(s) must be soluble in a suitable solubilizing media, either organic or inorganic. A preferred impregnating solution comprises an aqueous solution of ammonium metatungstate. The impregnation of the support may be carried out in one step utilizing the impregnating solution, or it may be carried out in a multi-step process, sequentially impregnating the material, drying, calcining, reimpregnating, drying, calcining, etc. A preferred impregnating process is the so-called "dry impregnation" when just a sufficient amount of impregnating solution is used such that all the pore volume in the carrier is filled and no excess solution is left after impregnation. After impregnation, the next step is to dry and calcine the impregnated material. The drying and calcining can be carried out in individual steps. For example, drying can be, carried out at a temperature ranging up to about 150° C. followed by calcining step at temperatures ranging from about 600° C. to about 800° C. Preferably, the drying and calcining are carried out in one continuous step, heating the material slowly through the low temperature ranges to dry the material and then raising the temperature to the calcining conditions. The purpose of the calcining is to convert the soluble tungsten salt to an oxide upon the support material. Calcining is carried out in an oxidizing atmosphere, air being a preferred atmosphere. Nitrogen is not a suitable alternative atmosphere. The drying step is preferably carried out in the initial stages of calcining step. Drying and calcining times are not critical and depend on temperatures. These are readily determined by simple experimentations. Five minutes to ten hours are usually sufficient, although longer times are acceptable.

The critical step in preparing a long-life catalyst for the alkylation of the benzene or benzene compounds in the instant process without concomitantly disproportionating the detergent range olefin feedstock comprises an activation of the catalyst in a neutral or reducing gaseous atmosphere at a temperature ranging from about 200° C. to about 400° C. after the catalyst has been calcined. The use of higher temperatures for activating produces a catalyst that not only alkylates but also disproportionates the olefin feedstock, resulting in an alkylation product having a wide range of molecular weights. Activation in an oxidizing atmosphere such as air diminishes the catalyst life.

The support utilized in the instant invention, i.e. containing 70 to 90% by weight of silica is critical for the successful operation of the instant process. Supports containing substantially alumina or substantially silica, or having less or more than 70–90% by weight of silica provide catalysts that are much less active than the catalysts utilized in the instant invention. Catalysts prepared of tungsten oxide on these alternative supports further have a much lower life than the catalysts of the instant invention. Also the latter catalysts produce large amounts of unwanted disproportionation products.

The tungsten oxide supported catalysts of this invention are used in typical fashion, for example, in packed beds, or in fluidized beds. In operation, a process stream containing benzene or a substituted benzene to be alkylated is combined with a process stream containing an olefin to be utilized for alkylation and passed over a catalyst bed at a temperature ranging from about 100° C. to about 350° C. and a pressure ranging from about 100 to about 2000 psig. An aromatic to olefin molar ratio of about 1:1 to about 20:1, preferably from about 2:1 to about 15:1 can be employed.

Upon completion of the reaction, the product obtained can be separated into its individual components by any simple means, such as for example, by distillation.

The invention will be described by the following examples which are provided for illustration and are not to be construed as limiting the invention.

ILLUSTRATIVE EMBODIMENT I

Catalyst Preparation

The following example describes a typical preparation of the catalysts used in the instant process.

30 Grams of Davison Grade 980-25 $SiO_2$ (75% silica—25% alumina, 20-30 mesh) are dried at 500° C. for 2 hours and cooled and dried by nitrogen. This material is dry impregnated with 20 milliliters of an impregnating solution prepared by dissolving 2.8 grams of ammonium metatungstate in 20 milliliters of distilled water. The impregnating material is dried for 0.5 hours at 100° C. and then calcined by passing air over the catalyst as it is heated to 500° C. over a period of 3 hours. The calcining material was then activated by sweeping it with a gaseous mixture of nitrogen and hydrogen with an $N_2/H_2$ ratio of 2:1 at 290° C. for 15 minutes. Analysis of the resultant catalyst shows it to contain about 6% by weight of tungsten.

ILLUSTRATIVE EMBODIMENT II

A series of catalysts containing various amounts of tungsten are prepared as described in Illustrative Embodiment I above. Approximately 5 grams of catalysts to be tested are placed in a vertical tubular reactor which is operated in an upflow manner. Benzene and 1-dodecene in the molar ratio of 10:1 is fed to the reactor. Reaction temperature is maintained at approximately 150° C. and the feed is maintained at an LHSV (liquid hourly space velocity) of about 18. The product from the reactor is analyzed and the results are obtained such as those shown in Table I below

TABLE I

| Example No. | Catalyst[a] % wt W | 1-DODECENE % CONV. | RELATIVE MOLAR % | | n-DODECYLBENZENE, ISOMER DISTRIBUTION[c] | | | | |
|---|---|---|---|---|---|---|---|---|---|
| | | | Dodecyl-Benzene | Didodecyl-Benzene | 1-PD[b] | 2-PD | 3-PD | 4-PD | 5+6—PD |
| I-1 | 16.8 | 96.8 | >92.2 | <7.8 | — | 27 | 22 | 18 | 33 |
| I-2 | 5.7 | 98.9 | 95.3 | 4.7 | — | 27 | 22 | 18 | 33 |
| I-3 | 3.0 | 98.9 | 96.4 | 3.6 | — | — | not measured | — | — |
| I-4 | 1.4 | 98.5 | 95.9 | 4.1 | — | — | not measured | — | — |
| I-5 | 0 | 85.5 | 94.3 | 5.7 | — | 43 | 25 | 14 | 18 |

[a] The catalysts are prepared by dry impregnation of the support with ammonium metatungstate; subsequently drying and calcining in air up to 700° C. These materials are then swept with a 2:1 $N_2/H_2$ mixture at 290° C. for 15 minutes before being used. In Example I-5, the silica alumina is calcined up to 700° C. as were the $WO_3/SiO_2$-$Al_2O_3$ catalysts, but is swept with $N_2$ only at 290° C. before use.

[b] PD is a phenyl-n-dodecane, e.g. 1-phenyldodecane, etc.

[c] By $^{13}C$ NMR analysis.

As can be seen from Table I above, while the silica-alumina support alone has an activity for alkylation of benzene, the addition of the tungsten oxide to the support significantly increases the conversion rate, to above 98%. With the tungsten supported catalysts one sees a very nice distribution of the alkylated dodecyl benzene, whereas with the silica-alumina support alone the distribution is skewed toward the 2-phenyldodecene.

ILLUSTRATIVE EMBODIMENT III

A series of catalysts are prepared as described in Illustrative Embodiment I above using various supports as shown in Table II below.

TABLE II

| Support | Composition | Manufacturer | Surface Area m²/g | Pore Volume cc/gm | Density gm/cc |
|---|---|---|---|---|---|
| II-1 | 75% $SiO_2$ 25% $Al_2O_7$ | Grade 980-25, Davison Chemical Div., W.R. Grace & Co. | 325 | 0.45 | 0.73 |
| II-2 | $Al_2O_3$ | Kaiser 201, Kaiser Aluminum & Chemical Corp. | 365 | 0.42 | — |
| II-3 | $SiO_2$ | Grade 57, Davison Chemical Div., W.R. Grace & Co. | 300 | 1.0 | 0.40 |
| II-4 | $Al_2O_3$ | Norton, Norton Company | 218 | 0.62 | — |
| II-5 | 87% $SiO_2$ 13% $Al_2O_3$ | Grade 980-13, Davison Chemical Div., W.R. Grace & Co. | 375 | 0.40 | 0.73 |

These materials are tested as described in Illustrative Embodiment II at a reaction temperature of 150° C. and at the feed rates listed in Table III below.

TABLE III

| Example No. | Catalyst[a] Support | % wt W | FEED LHSV | 1-DODE-CENE % CONV. | RELATIVE MOLAR % Dodecyl-Benzene | Dido-decyl-Benzene | n-DODECYLBENZENE, DISTRIBUTION[c] 1-PD[b] | 2-PD | 3-PD | 4-PD | 5+6—PD | OTHER PRODUCTS mole % of Total |
|---|---|---|---|---|---|---|---|---|---|---|---|---|
| III-1 | 75% $SiO_2$-25% $Al_2O_3$ Kaiser | 16.8 | 18 | 96.8 | >92.2 | <7.8 | — | 27 | 22 | 18 | 33 | ~0 |
| III-2 | 201 $Al_2O_3$ Davison | 16.8 | 18 | 68.7 | 94.5 | 5.5 | — | not measured — | — | — | — | ~0 |
| III-3 | 57 $SiO_2$ | 17.5 | 18 | 19.1 | 83.8 | e | — | not measured — | — | — | — | 16.2 |
| III-4 | 75% $SiO_2$-25% $Al_2O_3$ Davison | 5.7 | 18 | 98.9 | 95.3 | 4.7 | — | 27 | 22 | 18 | 33 | ~0 |
| III-5 | 57 $SiO_2$ Kaiser | 6.0 | 5 | 15.8 | 56.3 | e | — | not measured — | — | — | — | 43.7 |
| III-6 | 201 $Al_2O_3$ | 6.0 | 5 | 2.0 | 46.6 | e | — | not measured — | — | — | — | 53.4 |
| III-7 | 75% $SiO_2$-25% $Al_2O_3$ Norton | 3.0 | 18 | 98.9 | 96.4 | 3.6 | — | not measured — | — | — | — | — |
| III-8 | $Al_2O_3$ | 3.0 | 5 | 3.3 | 96.7 | 3.3 | — | not measured — | — | — | — | — |
| III-9 | 87% $SiO_2$ 13% $Al_2O_3$ | 6.0 | 18 | 84.7 | 96.1 | 3.9 | — | — | — | — | — | — |

[a]The catalysts are prepared by dry impregnation of the support with ammonium metatungstate; subsequently drying and calcining in air up to 700° C. The catalyst is finally activated at 290° C. with a 2:1 $N_2/H_2$ mixture for 15 minutes before being used.
[b]PD is a phenyl-n-dodecane, e.g. 1-phenyldodecane, etc.
[c]By $^{13}C$ NMR analysis.
[d]Primarily olefin disproportionation products and perhaps some olefin dimers.
e Large quantities and numbers of products interfered with didodecylbenzene analyses. These compounds are included in the column titled "Disproportionation Products".

As can be seen from the table above the use of supports other than the silica-alumina either gives low conversions of the 1-dodecene or provides a large number of disproportionation compounds in the endproduct.

ILLUSTRATIVE EMBODIMENT IV

A series of catalysts are prepared both according to this invention and not according to this invention to illustrate the importance of proper activation procedures. As a support, the Davison 980-25 silica alumina (75% silica–25% alumina) is utilized. The catalysts are prepared by dry impregnation of the supports with ammonium metatungstate. These impregnated materials are subsequently calcined in air up to 700° C. (except for Example IV-10 which was calcined only up to 500° C.). The catalysts are then swept with the activating gases as described in Table IV below. The activated catalysts are then tested as per Illustrative Embodiment II and the results are also provided in Table IV below.

TABLE IV

| Example No. | Catalyst % wt W | ACTIVATION CONDITIONS | RXN TEMP °C. | FEED LHSV | 1-DODECENE % CONV. | RELATIVE MOLAR % OF ALKYLATE PRODUCT Dodecyl-Benzene | Didodecyl-Benzene | OTHER PRODUCTS, mole[g] % of Total |
|---|---|---|---|---|---|---|---|---|
| IV-1 | 3.0 | $N_2+H_2$[a] 290° C. | 120 | 10 | 96.1 | 96.8 | 3.2 | ~0 |
| IV-2 | 3.0 | $N_2+H_2$[b] 350° C. | 120 | 10 | 97.9 | 95.9 | 4.1 | ~0 |
| IV-3 | 3.0 | $N_2+H_2$[c] 400° C. | 120 | 10 | 93.7 | 95.2 | 4.8 | 8.7 |
| IV-4 | 3.0 | $N_2+H_2$[d] 500° C. | 120 | 10 | 96.2 | 70 | h | ~25 |
| IV-5 | 5.7 | $N_2+H_2$[e] 300° C. | 150 | 10 | 98.8 | 94.5 | 5.5 | ~0 |
| IV-6 | 5.9 | $N_2$[f] 300° C. | 150 | 10 | 96.9 | 97.4 | 2.6 | 1.1 |

TABLE IV-continued

| Example No. | Catalyst % wt W | ACTIVATION CONDITIONS | RXN TEMP °C. | FEED LHSV | 1-DODECENE % CONV. | RELATIVE MOLAR % OF ALKYLATE PRODUCT | | OTHER PRODUCTS, mole$^g$ % of Total |
|---|---|---|---|---|---|---|---|---|
| | | | | | | Dodecyl-Benzene | Didodecyl-Benzene | |
| IV-7 | 5.9 | $N_2$$^f$ / 300° C. | 120 | 10 | 79.9 | 97.6 | 2.4 | 2.5 |
| IV-8 | 3 | $N_2$$^f$ / 400° C. | 120 | 10 | 76.0 | 98.4 | 1.6 | 1.7 |
| IV-9 | 3 | $N_2$$^f$ / 500° C. | 120 | 10 | 87.9 | 67 | h | 33 |
| IV-10 | 3 | air$^f$ / 500° C. | 120 | 10 | 81.1 | 97 | 3 | 3.3 |

$^a$Catalyst was swept with a 2:1 $N_2/H_2$ mixture at 290° C. for 15 minutes.
$^b$Catalyst was swept with a 2:1 $N_2/H_2$ mixture at 350° C. for 15 minutes.
$^c$Catalyst was swept with 2:1 $N_2/H_2$ mixture for 15 minutes at each temperature of 290° C., 350° C. and 400° C.
$^d$Catalyst was swept with 2:1 $N_2/H_2$ mixture for 15 minutes at each temperature of 290° C., 400° C. and 500° C.
$^e$Catalyst was swept with 2:1 $N_2/H_2$ mixture for 15 minutes at 300° C.
$^f$Catalyst was swept with nitrogen for 15 minutes.
$^g$Olefin disproportionation and dimerization products. Products other than dodecylbenzene and didodecylbenzene.
h Large quantities and numbers of products interfered with didodecylbenzene analysis. These compounds are included in the column titled "Other Products".

As can be seen from Table IV above, catalysts that are activated in a neutral or reducing atmosphere at a temperature ranging from about 200° C. to about 350° C. show a much more active catalyst with a higher selectivity to the dodecyl benzene than the catalysts that are activated at other temperatures.

ILLUSTRATIVE EMBODIMENT V

When catalysts prepared according to the instant invention and calcined in a neutral or reducing atmosphere at 200°-350°C. are compared with comparable catalysts calcined in air at the same temperature, the former catalysts are found to maintain their activity for a longer period of time than the latter catalysts.

ILLUSTRATIVE EMBODIMENT VI

A catalyst prepared as described in Illustrative Embodiment I above and containing 6 weight percent tungsten is placed in reactor and tested as described in Illustrative Embodiment II above. In this case, toluene is utilized as a feedstock with a toluene 1-dodecene molar ratio of 10. Reaction temperature ranges from about 120° C. to about 150° C., and the feed rate is an LHSV of about 10. The conversion of the 1-dodecene is about 90%, and the selectivity to the dodecyl toluene is 95% with 16% ortho, 19% meta and 65% para-dodecene toluene being present.

ILLUSTRATIVE EMBODIMENT VII

Using a catalyst as prepared in Illustrative Embodiment I above which contains 6% tungsten and testing this material as per Illustrative Embodiment II above, utilizing ortho-xylene and propylene tetramer as feedstock with a molar ratio of xylene to tetramer of about 10 to 1 and at a reaction temperature of about 150° C., the successful alkylation of ortho-xylene with a branched dodecene material is demonstrated.

I claim:

1. A process for alkylating benzene and lower alkyl-substituted benzenes with a detergent range olefin having a carbon number ranging from about 8 to about 22 which comprises contacting said benzene or lower alkyl-substituted benzene with said olefin in the presence of a catalyst comprising tungsten oxide supported on a porous silica-alumina support which support contains from about 70 to about 90% by weight of silica wherein said catalyst is prepared by impregnating the support with an aqueous solution of a tungsten salt, calcining the impregnated support in an oxidizing atmosphere at a temperature ranging from up to about 600° C. up to about 800° C. and subsequently activating the catalyst in a neutral or reducing gaseous atmosphere at a temperature ranging from up to about 200° C. up to about 350° C.

2. The process of claim 1 wherein lower alkyl substituents on the lower alkyl-substituted benzenes have carbon numbers ranging from 1 to 5.

3. The process of claim 2 wherein the carbon numbers range from 1 to 2.

4. The process of claim 3 where the lower alkyl-substituted benzene is toluene or xylene.

5. The process of claim 1 wherein the carbon number of the detergent range olefin ranges from about 10 to about 20.

6. The process of claim 1 wherein the alkylation temperature ranges from about 75° C. to about 250° C.

7. The process of claim 6 wherein the alkylation temperature ranges from about 100° C. to about 200° C.

8. The process of claim 1 wherein the weight percent of the tungsten oxide on the support ranges from about 0.5 to about 25 percent by weight basis tungsten metal.

* * * * *